United States Patent [19]
Bird

[11] Patent Number: 5,916,907
[45] Date of Patent: Jun. 29, 1999

[54] METHOD FOR PREVENTING OR TREATING LOW RENIN HYPERTENSION BY ADMINISTERING AN ENDOTHELIN ANTAGONIST

[75] Inventor: Joan Eileen Bird, Princeton, N.J.

[73] Assignee: Bristol-Myers Squibb Company, Princeton, N.J.

[21] Appl. No.: 09/014,434

[22] Filed: Jan. 27, 1998

Related U.S. Application Data

[60] Provisional application No. 60/035,825, Jan. 30, 1997.

[51] Int. Cl.$^6$ .................................................. A61K 31/42
[52] U.S. Cl. .............................................. 514/374
[58] Field of Search ............................................ 514/374

[56] References Cited

U.S. PATENT DOCUMENTS

| | | | |
|---|---|---|---|
| 2,888,455 | 5/1959 | Kano et al. | 260/239.9 |
| 4,415,496 | 11/1983 | Harris et al. | 260/239.38 |
| 4,661,479 | 4/1987 | Wyvratt, Jr. et al. | 514/214 |
| 4,749,688 | 6/1988 | Haslanger et al. | 514/19 |
| 5,236,928 | 8/1993 | Chakravarty et al. | 514/275 |
| 5,270,313 | 12/1993 | Burri et al. | 514/252 |
| 5,292,740 | 3/1994 | Burri et al. | 514/256 |
| 5,378,715 | 1/1995 | Stein et al. | 514/329 |
| 5,464,853 | 11/1995 | Chan et al. | 514/378 |
| 5,514,691 | 5/1996 | Chan et al. | 514/312 |
| 5,514,696 | 5/1996 | Murugesan et al. | 514/380 |
| 5,571,821 | 11/1996 | Chan et al. | 514/312 |
| 5,591,761 | 1/1997 | Chan et al. | 514/380 |
| 5,594,021 | 1/1997 | Chan et al. | 514/378 |
| 5,612,359 | 3/1997 | Murugesan | 514/365 |
| 5,760,038 | 6/1998 | Murugesan et al. | 514/252 |
| 5,780,473 | 7/1998 | Murugesan et al. | 514/252 |

FOREIGN PATENT DOCUMENTS

| | | |
|---|---|---|
| 34011/93 | 9/1993 | Australia. |
| 67357/94 | 1/1995 | Australia. |
| 48039/96 | 9/1996 | Australia. |
| 76072 | 4/1983 | European Pat. Off.. |
| 404525 | 12/1990 | European Pat. Off.. |
| 443983 | 8/1991 | European Pat. Off.. |
| 510526 | 10/1992 | European Pat. Off.. |
| 526708 | 2/1993 | European Pat. Off.. |
| 558258 | 9/1993 | European Pat. Off.. |
| 569193 | 11/1993 | European Pat. Off.. |
| 601386 | 6/1994 | European Pat. Off.. |
| 617001 | 9/1994 | European Pat. Off.. |
| 626174 | 11/1994 | European Pat. Off.. |
| 633259 | 1/1995 | European Pat. Off.. |
| 634175 | 1/1995 | European Pat. Off.. |
| 640596 | 3/1995 | European Pat. Off.. |
| 682016 | 11/1995 | European Pat. Off.. |
| 702012 | 3/1996 | European Pat. Off.. |
| 725067 | 8/1996 | European Pat. Off.. |
| 749964 | 12/1996 | European Pat. Off.. |
| 0364506 | 11/1962 | Switzerland. |
| 804036 | 11/1958 | United Kingdom. |
| 1473433 | 5/1977 | United Kingdom. |
| 2228933 | 9/1990 | United Kingdom. |
| 91/15479 | 10/1991 | WIPO. |
| 93/08799 | 5/1993 | WIPO. |
| 93/10094 | 5/1993 | WIPO. |
| 93/23404 | 11/1993 | WIPO. |
| 94/27979 | 12/1994 | WIPO. |
| 95/26957 | 10/1995 | WIPO. |
| 96/31492 | 10/1996 | WIPO. |
| 96/40681 | 12/1996 | WIPO. |

OTHER PUBLICATIONS

Bird et al., Hypertension, vol. 25, Jun. 1995, p. 1191–1195.
S. Norio et al., Chemical Abstracts, vol. 70, No. 19, (1969), 87639g.
T. Saito, Chemical Abstracts, vol. 73, No. 23 (1970), 120511w.
Derwent Abstract No. 88–289069/41 Feb. 27, 1987.
Derwent Abstract No. 88–195835/28 Nov. 26, 1986.
Derwent Abstract No. 88–061295/09 Jul. 9, 1986.
Derwent Abstract No. 87–152485/22 Oct. 11, 1985.
Derwent Abstract No. 62299 E/30 Dec. 11, 1980.
Derwent Abstract No. 40927 D/23 Sep. 11, 1979.
Derwent Abstract No. 91–254550/35 Feb. 19, 1990.
Derwent Abstract No. 86–246709/38 Nov. 27, 1985.
Derwent Abstract No. 35012 K/15 Sep. 24, 1981.
Allen et al., CA116(11):106284Z, p. 778, 1992.
R.D. Desai et al., Chemical Abstracts, vol. 71, No. 11, (1969) 49825c.
R.D. Desai et al., Chemical Abstracts, vol. 71, No. 3, (1969) 12872q.
P. G. Ferrini et al., Angew. Chem. Internat. Edit., vol. 2, No. 2 (1963) p. 99.
A. M. van Leusen, et al., "Synthesis . . . Compounds", J. Org. Chem., vol. 41, No. 4, (1976), pp. 69–71.
W. J. Hammar et al., J. Heterocyclic Chem., vol. 18, (1981) pp. 885–888.
A. M. van Leusen et al., Tetrahedron Letters, No. 23, (1972), pp. 2369–2372.
Chan et al., "Identification of a New Class of $ET_A$ Selective Endothelin Antagonists by Pharmacophore Directed Screening", Biochemical and Biophysical Research Communications, vol. 201, No. 1, May 30, 1994, pp. 228–234.
Stein et al., "The Discovery of Sulfonamide Endothelin Antagonists and the Development of the Orally Active $ET_A$ Antagonist 5–(Dimethylamino)–N–(3, 4–dimethyl–5–isoxazolyl)–1–naphthalenesulfonamide", J. Med. Chem., vol. 37, No. 3, Feb. 4, 1994, pp. 329–331.
Doherty, J. Med. Chem., 35(9), 1493–1508 (May 1992).
CA 65: 2241d (1966).
CA 92:41908v (1979).
Wang et al., "Nitrile . . . sinomin," CA 108:94444w, p. 651 (1988).
Khanna, "Oral . . . formulation," CA 115:35728p, p. 415 (1991).

(List continued on next page.)

Primary Examiner—Phyllis Spivack
Attorney, Agent, or Firm—Suzanne E. Babajko; Stephen B. Davis

[57] ABSTRACT

Prevention or treatment of low renin hypertension by administration of an endothelin antagonist is disclosed.

2 Claims, No Drawings

OTHER PUBLICATIONS

Stein et al., "The Discovery . . . 1–naphthalenesulfonamide," CA 120:18233n, p. 21–22 (1994).

Vree et al., "Renal excretion . . . function," CA 97:84685r, p. 23 (1982).

Oie, "Pharmacokinetics . . . dosing," CA102:197512x, p. 18 (1985).

Murugesan et al., "N–(heteroaryl) . . . antagonists," CA 120:270370c, p. 1067 (1994).

Ihara et al., Life Sciences, vol. 50, pp. 247–255 (1991).

Reynolds et al., The Journal of Pharmacology and Experimental Therapeutics, vol. 273(3), 1410–1417 (1995).

Williams et al., The Journal of Pharmacology and Experimental Therapeutics, vol. 275(3), 1518–1526 (1995).

Ohlstein et al., Proc. Natl. Acad. Sci., vol. 91, pp. 8052–8056 (1994).

Ohlstein et al., The Journal of Pharmacology and Experimental Therapeutics, vol. 276(2), 609–615 (1996).

Opgenorth et al., The Journal of Pharmacology and Experimental Therapeutics, vol. 276(2), 473–481 (1996).

Masuda et al., The Journal of Pharmacology and Experimental Therapeutics, vol. 279(2), 675–685 (1996).

Clozel et al., The Journal of Pharmacology and Experimental Therapeutics, vol. 270(1), 228–235 (1994).

Ergul et al., Hypertension, pp. 652–655 (Oct. 1996).

King, A. J., B. M. Brenner, and S. Anderson. Endothelin: a potent renal and systemic vasoconstrictor peptide. Am. J. Physiol. 256:F1051–1058, 1989.

Cao, L. and R. O. Banks. Cardiorenal actions of endothelin, Part I: Effects of converting enzyme inhibition. Life Sci. 46:577–583, 1990.

Cargnelli, G., G. Rossi, S. Bova and A. C. Pessina. In vitro vascular reactivity to endothelin: A comparison between young and old normotensive and hypertensive rats. Clin. and Exper. Hyper.–Theory and Practice. A12(8):1437–1451, 1990.

Tomobe, Y. T. Miyauchi, A. Saito, M. Yanigasawa, S. Kimura, K. Goto and T. Masaki. Effects of endothelin on the renal artery from spontaneously hypertensive and Wistar Kyoto rats. Eur. J. Pharmac. 152: 373–374, 1988.

Suzuki, N., T. Miyauchi, Y. Tomobe, H. Matsumoto, K. Goto, T. Masaki, and M. Fujino. Plasma concentrations of endothelin–1 in spontaneously hypertensive rats and DOCA–salt hypertensive rats. Bioc. Bioph. Res. Comm. 167(3):941–947, 1990.

Goligorsky, M. S., K. Iijima, M. Morgan, M. Yanigasawa, T. Masaki, L. Lin, A Nasjletti, M. Frazer, and K. Badr. Role of endothelin in the development of Dahl hypertension. J. Vasc. Med. and Biol. 2(4): 185A, 1990.

McMahon, E.G., Palomo, M.A., Moore, W.M., J. Cardiovasc. Pharmacol.; 17 Supp 7: S29–33 (1991).

METHOD FOR PREVENTING OR TREATING LOW RENIN HYPERTENSION BY ADMINISTERING AN ENDOTHELIN ANTAGONIST

This application claims priority from provisional U.S. application Ser. No. 60/035,825, filed Jan. 30, 1997, incorporated herein by reference in its entirety.

FIELD OF THE INVENTION

The present invention relates to the prevention or treatment of low renin hypertension by administering an endothelin antagonist.

BRIEF DESCRIPTION OF THE INVENTION

Hypertension has a variety of etiologies. Due at least in part to this, the success of a pharmacological agent in treating one form of hypertension does not necessarily indicate that that agent will be successful in treating another form of hypertension.

One major contributor to hypertension is the "renin cascade", which culminates in the production of the potent vasoconstrictor angiotensin II. Renin is a protease which cleaves angiotensinogen to form angiotensin I, the latter which is then cleaved by a second enzyme (the angiotensin-converting enzyme or ACE) to form angiotensin II. Administration of a pharmacological agent which inhibits renin or ACE, or which antagonizes the angiotensin II end-product of the cascade ("AII antagonist"), can lower blood pressure and provide a route for the treatment of this form of hypertension ("essential hypertension") which affects a large portion of the hypertensive patient population.

Some individuals, however, have low levels of plasma-renin concentration or low plasma-renin activity, yet manifest hypertension. This form of hypertension, often found in the African-American community and in the elderly, is referred to as "low renin hypertension" (or "sodium and volume dependent low renin hypertension" as sodium down-regulates the renin system). In these individuals, increased sodium intake is followed by an increase in blood pressure despite the fact that renin plasma concentrations are maintained or lowered. Agents active in treating essential hypertension, such as ACE inhibitors or AII antagonists, are relatively ineffective in treating low renin hypertension. The art has thus continued to search for agents effective in the treatment of hypertension of such different etiologies.

Endothelin antagonists, which are compounds capable, inter alia, of inhibiting the binding of endothelin peptides to endothelin receptors, are useful in the treatment of endothelin-related disorders. While certain such compounds have been described as having utility in the treatment of hypertension, the present invention provides a method employing these compounds specifically for the treatment of low renin hypertension.

DETAILED DESCRIPTION OF THE INVENTION

The present invention provides a method for the prevention or treatment of low renin hypertension in a mammal, comprising administering an endothelin antagonist to said mammal in an amount effective therefor.

The endothelin antagonist employed may be any compound capable of inhibiting the action of endothelin peptides, especially, endothelin-1 (ET-1), endothelin-2 (ET-2) and/or endothelin-3 (ET-3). The endothelin antagonists described in the following documents, incorporated herein by reference in their entirety, are exemplary of those contemplated for use in the present method: U.S. Pat. No. 5,378,715; U.S. Pat. No. 5,514,696; U.S. Pat. No. 5,420,123; U.S. application Ser. No. 114,251, filed Aug. 30, 1993; U.S. application Ser. No. 08/728,238, filed Oct. 8, 1996; European Patent Application 702,012; U.S. application Ser. No. 08/754,715, filed Nov. 21, 1996; U.S. application Ser. No. 08/692,869, filed Jul. 25, 1996, now U.S. Pat. No. 5,780,473, U.S. application Ser. No. 60/011,974, filed Feb. 20, 1996; U.S. application Ser. No. 60/013,491, filed Mar. 12, 1996; U.S. application Ser. No. 60/015,072, filed Apr. 9, 1996; World Patent Application 94/27979; U.S. Pat. No. 5,543,521; U.S. Pat. No. 5,464,853; U.S. Pat. No. 5,514,691; WO 96/06095; WO 95/08550; WO 95/26716; WO 96/11914; WO 95/26360; EP 601386; EP 633259; US 5,292,740; EP 510526; EP 526708; WO 93/25580; WO 93/23404; WO 96(04905; WO 94/21259; GB 2276383; WO 95/03044; EP 617001; U.S. Pat. No. 5,334,598; WO 95/03295; GB 2275926; WO 95/08989; GB 2266890; EP 496452; WO 94/21590; WO 94/21259; GB 2277446; WO 95/13262; WO 96/12706; WO 94/24084; WO 94/25013; U.S. Pat. No. 5,571,821; WO 95/04534; WO 95/04530; WO 94/02474; WO 94/14434; WO 96/07653; WO 93/08799; WO 95/05376; WO 95/12611; DE 4341663; WO 95/15963; WO 95/15944; EP 658548; EP 555537; WO 95/05374; WO 95/05372; U.S. Pat. No. 5,389,620; EP 628569; JP 6256261; WO 94/03483; EP 552417; WO 93/21219; EP 436189; WO 96/11927; JP 6122625; JP 7330622; WO 96/23773; WO 96/33170; WO 96/15109; WO 96/33190; U.S. Pat. No. 5,541,186; WO 96/19459; WO 96/19455; EP 713875; WO 95/26360; WO 96/20177; JP 7133254; WO 96/08486; WO 96/09818; WO 96/08487; WO 96/04905; EP 733626; WO 96/22978; WO 96/08483; JP 8059635; JP 7316188; WO 95/33748; WO 96/30358; U.S. Pat. No. 5,559,105; WO 95/35107; JP 7258098; U.S. Pat. No. 5,482,960; EP 682016; GB 2295616; WO 95/26957; WO 95/33752; EP 743307; and WO 96/31492; such as the following compounds described in the recited documents: BQ-123 (Ihara, M., et al., "Biological Profiles of Highly Potent Novel Endothelin Antagonists Selective for the $ET_A$ Receptor", *Life Sciences,* Vol. 50(4), pp. 247–255 (1992)); PD 156707 (Reynolds, E., et al., "Pharmacological Characterization of PD 156707, an Orally Active $ET_A$ Receptor Antagonist", *The Journal of Pharmacology and Experimental Therapeutics,* Vol. 273(3), pp. 1410–1417 (1995)); L-754,142 (Williams, D. L., et al., "Pharmacology of L-754,142, a Highly Potent, Orally Active, Nonpeptidyl Endothelin Antagonist", *The Journal of Pharmacology and Experimental Therapeutics,* Vol. 275(3), pp. 1518–1526 (1995)); SB 209670 (Ohlstein, E. H., et al., "SB 209670, a rationally designed potent nonpeptide endothelin receptor antagonist", *Proc. Natl. Acad. Sci. USA,* Vol. 91, pp. 8052–8056 (1994)); SB 217242 (Ohlstein, E. H., et al., "Nonpeptide Endothelin Receptor Antagonists. VI:Pharmacological Characterization of SB 217242, A Potent and Highly Bioavailable Endothelin Receptor Antagonist", *The Journal of Pharmacology and Experimental Therapeutics,* Vol. 276(2), pp. 609–615 (1996)); A-127722 (Opgenorth, T. J., et al., "Pharmacological Characterization of A-127722: An Orally Active and Highly Potent $ET_A$-Selective Receptor Antagonist", *The Journal of Pharmacology and Experimental Therapeutics,* Vol. 276(2), pp.473–481 (1996)); TAK-044 (Masuda, Y., et al., "Receptor Binding and Antagonist Properties of a Novel Endothelin Receptor Antagonist, TAK-044 {Cyclo[D-α-Aspartyl-3-[(4-Phenylpiperazin-1-yl)Carbonyl]-L-Alanyl-L-α-Aspartyl-D-2-(2-Thienyl) Glycyl-L-Leucyl-D-Tryptophyl]Disodium Salt}, in Human Endothelin$_A$ and Endothelin$_B$ Receptors", *The Journal of Pharmacology and Experimental Therapeutics,* Vol. 279(2), pp. 675–685 (1996)); bosentan (Ro 47-0203, Clozel, M., et al., "Pharmacological Characterization of Bosentan, A New Potent Orally Active Nonpeptide Endothelin Receptor Antagonist", *The Journal of Pharmacology and Experimental Therapeutics,* Vol. 270(1), pp. 228–235 (1994)); and TBC-11251, i.e.:

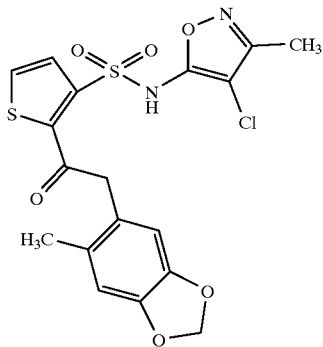

(IBC International Conference on Endothelin Inhibitors, Coronado, Calif. (February 1996) and 211th American Chemical Society National Meeting, New Orleans, La. (March 1996)). These exemplary compounds may, for example, be prepared by methods, and employed at dosages, such as those described in the aforementioned documents.

Endothelin antagonists containing a sulfonamide moiety (—SO$_2$—NH—) are preferred, particularly those described in European Patent Application 702,012, U.S. application Ser. No. 08/754,715, filed Nov. 21, 1996, and U.S. application Ser. No. 60/035,832, filed Jan. 30, 1997 by N. Murugesan et al., entitled "Endothelin Antagonists: N-[[2'-[[(4,5-Dimethyl-3-isoxazolyl)amino]sulfonyl]-4-(2-oxazolyl)[1,1'-biphenyl]-2-yl]methyl]-N,3,3-trimethylbutanamide and N-(4,5-Dimethyl-3-isoxazolyl)-2'-[(3,3-dimethyl-2-oxo-1-pyrrolidinyl)methyl]-4'-(2-oxazolyl)[1,1'-biphenyl]-2-sulfonamide and Salts Thereof" (Attorney Docket No. HA699*). Especially preferred are the following compounds:

N-(3,4-dimethyl-5-isoxazolyl)-4'-(2-oxazolyl)[1,1'-biphenyl]-2-sulfonamide, having the structure:

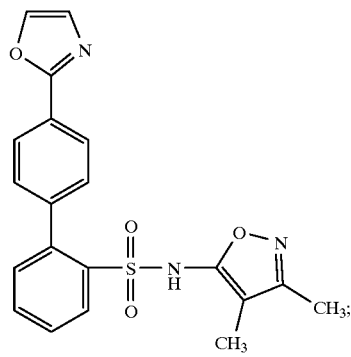

N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide, having the structure:

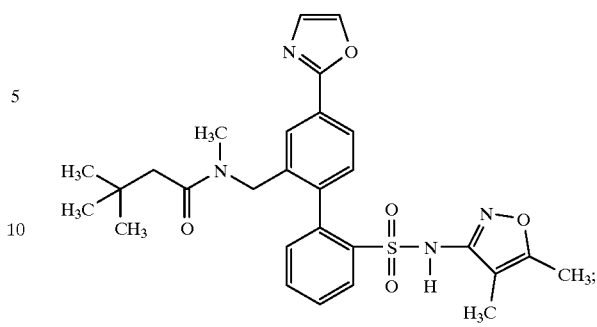

and pharmaceutically acceptable salts thereof. These preferred endothelin antagonists, and particularly the two especially preferred compounds shown above, are described as having a number of utilities such as the treatment of congestive heart failure and hypertension in U.S. Pat. No. 5,612,359 and U.S. application Ser. No. 60/035,832, filed Jan. 30, 1997, wherein the complete recitation of all these utilities is incorporated herein by reference; these preferred endothelin antagonists may be employed for each of these utilities alone or in combination with an agent such as an angiotensin II (AII) receptor antagonist (including irbesartan, 2-n-butyl-4-spirocyclopentane-1-[(2'-(tetrazol-5-yl)biphenyl-4-yl)methyl]-2-imidazolin-5-one).

The mammal may be any mammal subject to this malady, especially, a human. The endothelin antagonist may be administered in any suitable manner such as orally or parenterally, in an effective amount, such as within a dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The present invention also provides pharmaceutical compositions for the prevention or treatment of low renin hypertension, comprising an endothelin antagonist in an amount effective therefor and a pharmaceutically acceptable vehicle or diluent. The endothelin antagonist can be utilized in a composition such as tablet, capsule, sterile solution or suspension, compounded in a conventional manner with a physiologically acceptable vehicle or carrier, excipient, binder, preservative, stabilizer, flavor, etc. as called for by accepted pharmaceutical practice.

In the methods and compositions of the present invention, the endothelin antagonist may, for example, be employed alone, in combination with one or more other endothelin antagonists, or with another compound useful for the treatment of low renin hypertension, such as neutral endopeptidase (NEP) inhibitors, for example, candoxatril and acetorphan; dual NEP-ACE inhibitors such as [4S-[4α(R*), 7α, 10αβ]]-octahydro-4-(2-mercapto-1-oxo-3-phenylpropyl) amino]-5-oxo-7H-pyrido[2,1-b][1,3]thiazepine-7-carboyxlic acid (BMS-186716, U.S. Pat. No. 5,508,272), [S-(R*,R*)]-hexahydro-6-[(2-mercapto-1-oxo-3-phenylpropyl)amino]-2,2-dimethyl-7-oxo-1H-azepine-1-acetic acid (BMS-189921, U.S. Pat. No. 5,552,397), alatriopril, sampatrilat, MDL 100240, and CGS 30440; diuretics, such as chlorothiazide, hydrochlorothiazide, flumethiazide, hydroflumethiazide, bendroflumethiazide, methylchlorothiazide, trichloromethiazide, polythiazide and benzothiazide as well as ethacrynic acid, tricrynafen, chlorthalidone, furosemide, musolimine, bumetanide, triamterene, amiloride and spironolactone and salts of such compounds; and calcium entry blockers such as amlodipine.

If formulated as a fixed dose, such combination products preferably employ the endothelin antagonists within the dosage range described above and the other pharmaceutically active agent within its approved dosage range.

What is claimed is:

1. A method for preventing or treating low renin hypertension in a mammal, comprising administering to said mammal an endothelin antagonist in an amount effective therefor wherein said endothelin antagonist is the compound N-(3,4-dimethyl-5-isoxazolyl)-4'-(2-oxazolyl)[1,1'-biphenyl]-2-sulfonamide or a pharmaceutically acceptable salt thereof.

2. A method for preventing or treating low renin hypertension in a mammal, comprising administering to said mammal an endothelin antagonist in an amount effective therefor wherein said endothelin antagonist is the compound N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide or a pharmaceutically acceptable salt thereof.

* * * * *